United States Patent [19]

Duffett

[11] Patent Number: Plant 5,408

[45] Date of Patent: Feb. 26, 1985

[54] CHRYSANTHEMUM PLANT NAMED CHARDONNAY

[75] Inventor: William E. Duffett, Salinas, Calif.

[73] Assignee: Yoder Brothers, Inc., Barberton, Ohio

[21] Appl. No.: 504,730

[22] Filed: Jun. 16, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Chardonnay having the combined characteristics of flat capitulum form; daisy capitulum type; white ray floret color; diameter across face of capitulum ranging from 70 to 90 mm. at maturity; uniform nine week photoperiodic flowering response to short days; tall plant height when grown as a single stem spray cut mum; 85 to 110 mm. peduncles on open, normally terminal sprays; slow development of light green discs; and 13° C. minimum temperature tolerance for initiation and development of flowering buds.

3 Drawing Figures

The present invention comprises a new and distinct cultivar of *Chrysanthemum morifolium,* Ramat., named Chardonnay.

Chardonnay is a product of a planned sport induction program which had the objective of creating a new white chrysanthemum cultivar that would round out the color range of the Charisma family while retaining all other original traits.

Chardonnay was discovered and selected by William E. Duffett on Mar. 16, 1981 in a controlled environment in Salinas, Calif. as one flowering plant, a color variant within a flowering block established as rooted cuttings from stock plants which had been exposed as unrooted cuttings to an X-ray source of 1600 rads. The irradiated selection was a sectorial chimera derived from irradiation of Charisma, disclosed in U.S. Plant Pat. No. 4,561 and originated by the present inventor.

The first act of asexual reproduction of Chardonnay was accomplished when vegetative cuttings were taken from the initial selection in June, 1981 in a controlled environment in Salinas, Calif. by a technician working under formulations established and supervised by William E. Duffett.

Horticultural examination of selected units initiated June 1981 has demonstrated that the combination of characteristics as herein disclosed for Chardonnay are firmly fixed and are retained through successive generations of asexual reproduction.

Chardonnay has not been observed under all possible environmental conditions. The phenotype may vary significantly with variations in environment such as temperature, light intensity, and day length. The following observations, measurements and comparisons describe plants grown in Salinas, Calif. and Leamington, Canada under greenhouse conditions which approximate those generally used in commercial practice.

The following traits have been repeatedly observed and are determined to be basic characteristics of Chardonnay which in combination distinguish this chrysanthemum as a new and distinct cultivar:

(1) flat capitulum form:

(2) daisy capitulum type;

(3) white ray floret color;

(4) diameter across face of capitulum ranging from 70 to 90 mm. at maturity;

(5) uniform nine week photoperiodic flowering response to short days;

(6 ) medium peduncle length, ranging from 85 to 110 mm.;

(7) tall plant height, requiring 1 to 2 long day weeks prior to short days to attain a flowered plant height of 80 to 90 cm. for May through October flowerings; and (8) low temperature tolerance of 13° C. for initiation and development when grown in single stem cut spray programs with a continuous dark period of 13 to 14 hours.

The accompanying photographic drawings show typical inflorescence and foliage characteristics of Chardonnay, with the colors being as nearly true as possible with illustrations of this type. Sheet 1 is a color photograph of Chardonnay grown as a single stem cut spray. Sheet 2 is a black and white photograph of three views of the inflorescence of Chardonnay. Sheet 3 is a black and white photograph showing the leaves of Chardonnay at three stages of development (mature, intermediate and immature).

Of the many commercial cultivars known to the present inventor, the most similar in comparison to Chardonnay is White Marble, an unpatented but commercial cultivar. Reference is made to attached Chart A which compares certain characteristics of Chardonnay to those same characteristics of White Marble.

In comparison to White Marble, Chardonnay has a larger diameter across face of capitulum, taller plant height, shorter peduncle length, and is normally 6 days faster in flowering response time. The ray floret color, capitulum form, capitulum type and low temperature tolerance are similar.

In the following description, color references are made to The Royal Horticultural Society Colour Chart. The color values were determined between 9:00 A.M. and 9:30 A.M. on Feb. 15, 1983 under 150 foot-candle light intensity at Salinas, Calif.

CLASSIFICATION

Botanical: *Chrysanthemum morifloium,* Ramat., CV Chardonnay.

Commercial: Daisy spray cut mum.

INFLORESCENCE

Capitulum:

*Form.*—Flat.

*Type.*—Daisy.

*Diameter across face.*—70 To 90 mm.

Corolla of ray florets:

*Color (general tonality from a distance of three meters).*—White.

*Color (abaxial).*—155D.

*Color (adaxial).*—155B.

*Shape.*—Oblong. Pointed tip.

Corolla of disc florets:

*Color (mature).*—1A.

*Color (immature).*—154A.

Reproductive organs:

*Androecium.*—Present disc florets only; scant pollen.

*Gynoecium.*—Present both ray and disc florets.

PLANT

General appearance:

*Height.*—Tall; 80 to 90 cm., as a flowering plant from a rooted cutting, with seven long days for May through October flowerings and maintaining a minimum nightly 14 hour continuous dark period.

Foliage:

*Color (abaxial).*—147A.

*Color (adaxial).*—147B.

*Shape.*—Deeply lobed and coarsely serrated.

CHART A

COMPARISON OF CHARDONNAY AND WHITE MARBLE

| CULTIVAR | RAY FLORET COLOR | CAPITULUM FORM AND TYPE | SPRAY FORMATION |
|---|---|---|---|
| CHARDONNAY | WHITE | FLAT DAISY | 85 to 110 mm. PEDUNCLES |
| WHITE MARBLE | WHITE | FLAT DAISY | 150 to 200 mm. PEDUNCLES |

| CULTIVAR | DIAMETER ACROSS FACE OF CAPITULUM | PLANT HEIGHT | FLOWERING RESPONSE PERIOD |
|---|---|---|---|
| CHARDONNAY | 70 to 90 mm. | TALL 80 to 90 cm. | EARLY NINE WEEKS |
| WHITE MARBLE | 60 to 70 mm. | MEDIUM 60 to 70 cm. | LATE NINE WEEKS |

COMPARISONS MADE OF PLANTS GROWN AS SINGLE STEM SPRAY CUT MUMS WITH 7 LONG DAYS IN SALINAS, CALIFORNIA AND LEAMINGTON, CANADA

I claim:

1. A new and distinct plant of *Chrysanthemum morifolium,* Ramat., named Chardonnay, as described and illustrated, and particularly characterized as to uniqueness by the combined characteristics of flat capitulum form; daisy capitulum type; white ray floret color; diameter across face of capitulum ranging from 70 to 90 mm. at maturity; uniform nine week flowering response; tall plant height when grown single stem; 85 to 110 mm. peduncles on open, normally terminal sprays; slow development of light green discs; and 13° C. minimum temperature tolerance for initiation and development of flowering buds.

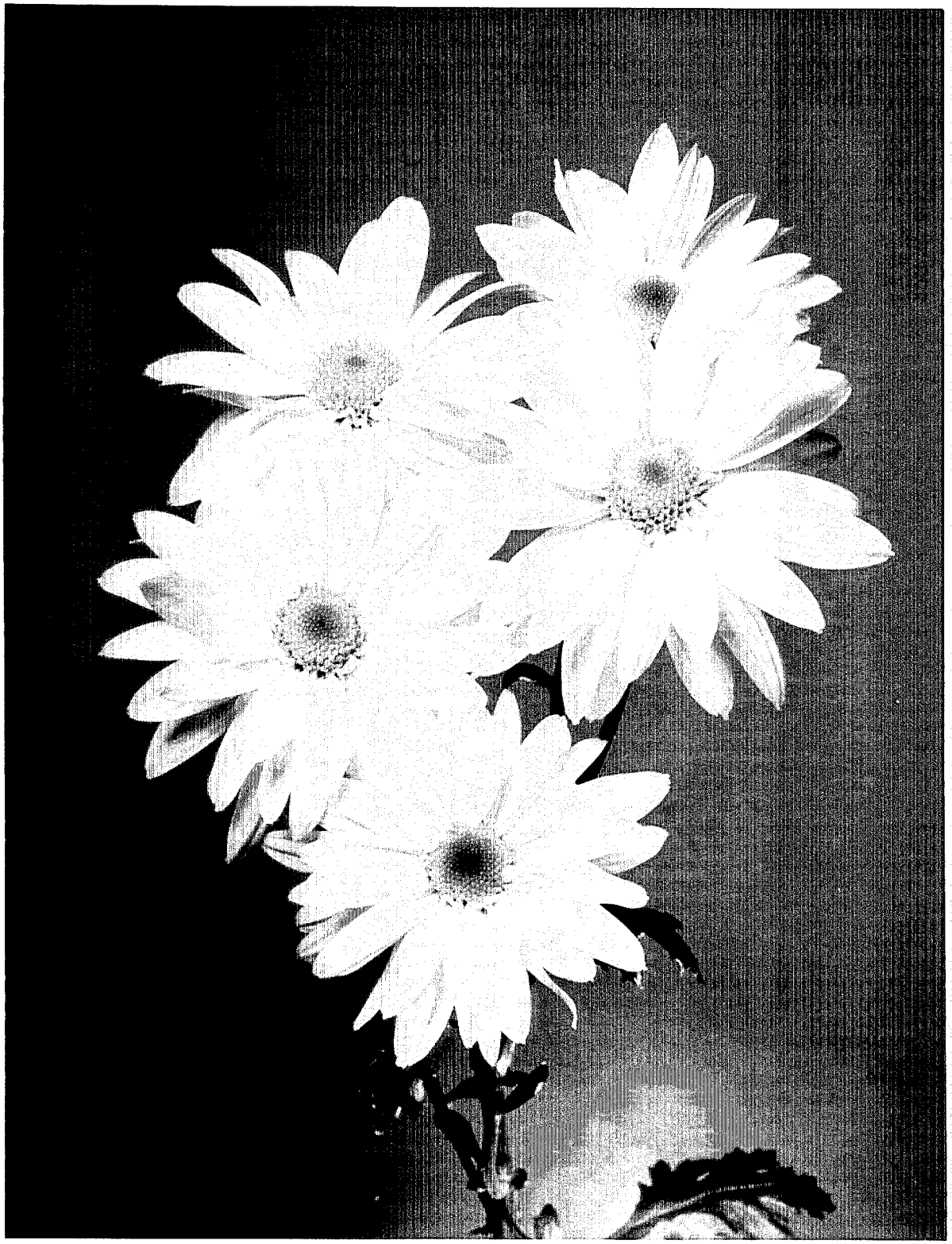

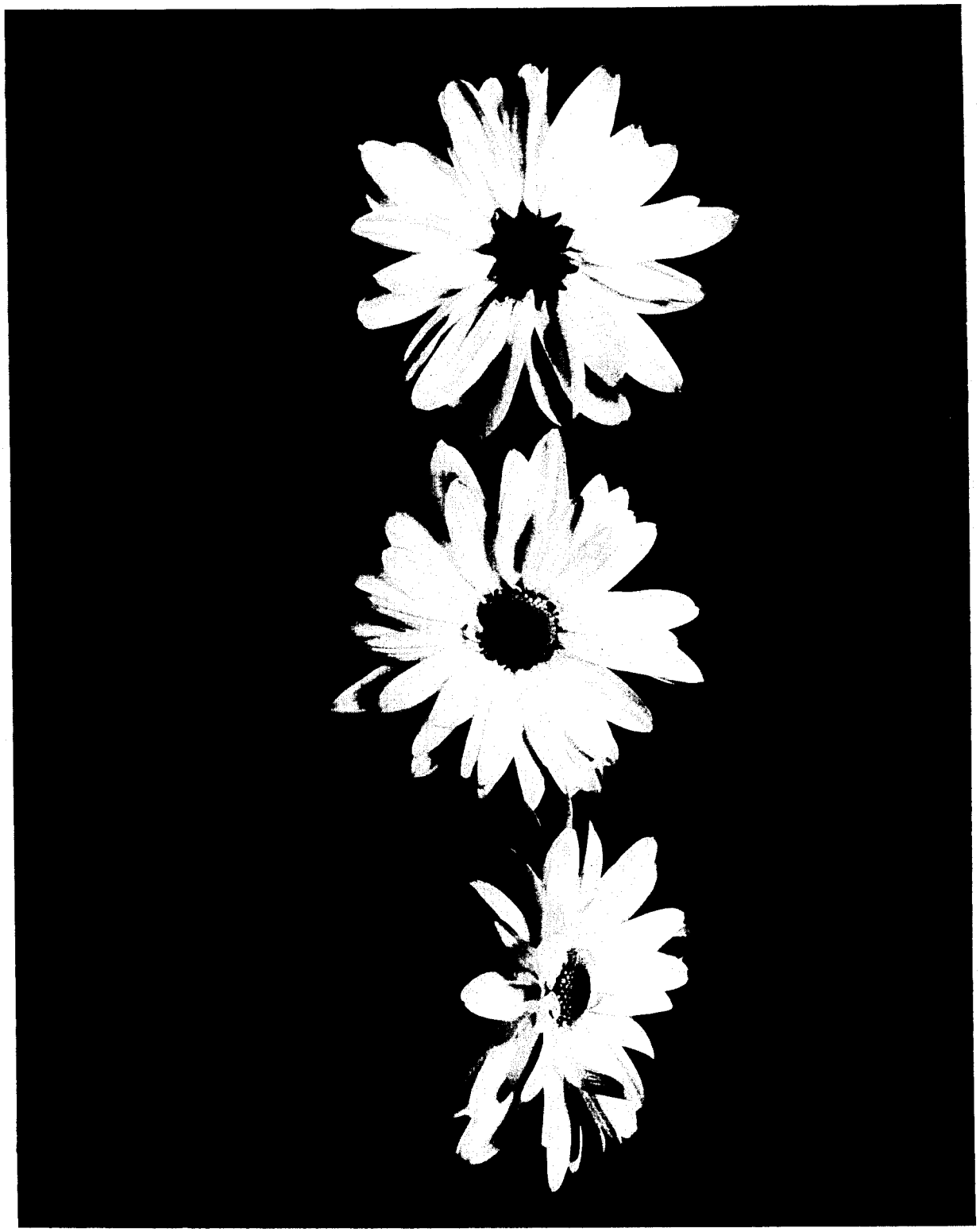

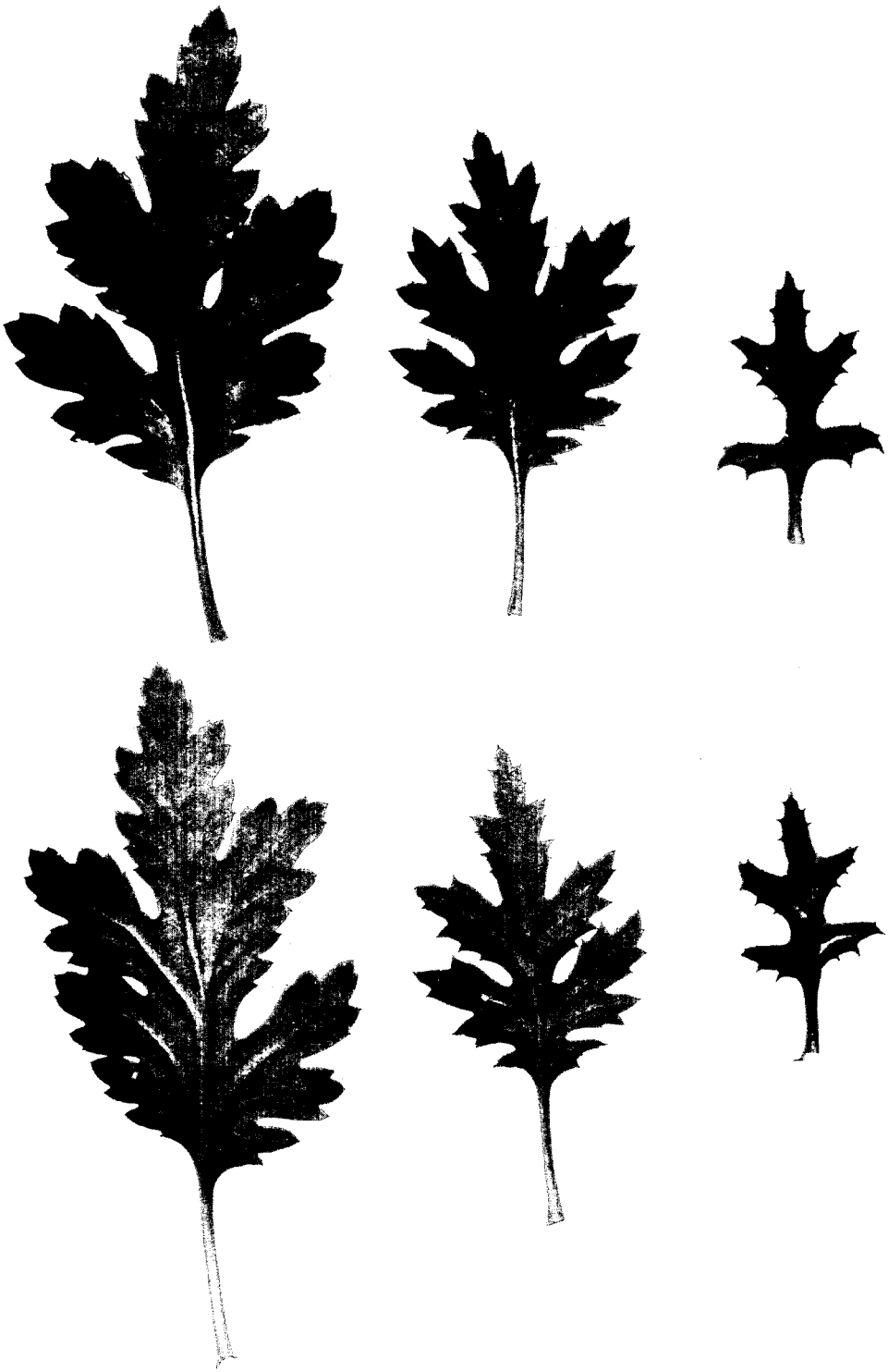

* * * * *